United States Patent [19]

Kramann

[11] Patent Number: 4,615,331

[45] Date of Patent: Oct. 7, 1986

[54] MEDICAL INSTRUMENTS WITH AID TO INTRODUCTION

[75] Inventor: Bernhard Kramann, Munich, Fed. Rep. of Germany

[73] Assignee: Sterimed Gesellschaft für medizinischen Bedarf mbH, Saarbrücken, Fed. Rep. of Germany

[21] Appl. No.: 709,024

[22] PCT Filed: Jun. 27, 1984

[86] PCT No.: PCT/EP84/00194

§ 371 Date: Feb. 26, 1985

§ 102(e) Date: Feb. 26, 1985

[87] PCT Pub. No.: WO85/00097

PCT Pub. Date: Jan. 17, 1985

[30] Foreign Application Priority Data

Jun. 28, 1983 [CH] Switzerland ............... 3526/83
Aug. 12, 1983 [DE] Fed. Rep. of Germany ....... 3329176

[51] Int. Cl.$^4$ .............................................. A61B 1/00
[52] U.S. Cl. ........................................ 128/4; 604/198
[58] Field of Search ........................... 128/4, 5, 6, 7; 604/198

[56] References Cited

U.S. PATENT DOCUMENTS 3,525,329 8/1970 Zeimer et al. ............... 128/4 X
4,321,915 3/1982 Leighton et al. ............ 128/4

*Primary Examiner*—William H. Grieb
*Attorney, Agent, or Firm*—Toren, McGeady, Stanger, Goldberg & Kiel

[57] ABSTRACT

An elongated medical instrument for the examination or treatment of body cavities, in particular endoscopes, with a device to assist introduction by the principle of the tubular structure which becomes everted is described, which instrument comprises the device to assist introduction 1 being composed of a pipe 2 which is open at both ends and has pressure connectors 3 on the sides, and is composed of a flexible, eversible tubular structure 4 running through the pipe 2, the two ends 5, 6 of the tubular structure each being connected to one end 7, 8 of the pipe 2, the medical instrument 9 running through the pipe 2 inside the tubular structure 4, and the tubular structure 4 being folded in several double-layers in the region 10 of the distal end 11 of the medical instrument 9.

1 Claim, 3 Drawing Figures

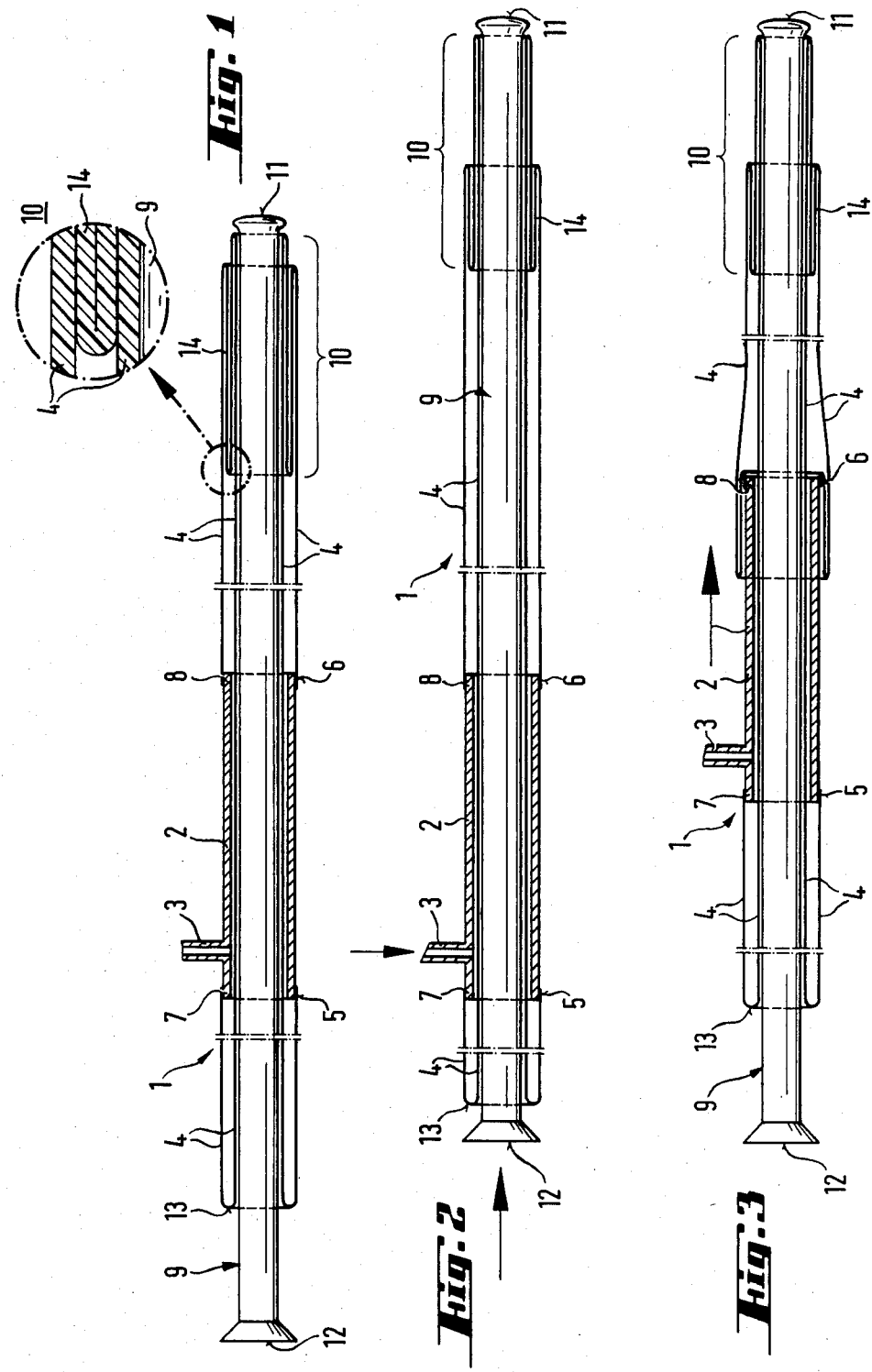

MEDICAL INSTRUMENTS WITH AID TO INTRODUCTION

FIELD OF THE INVENTION

The invention relates to an elongated, flexible medical instrument for the examination or treatment of body cavities, in particular endoscopes, with a device to assist introduction by the principle of the tubular structure which becomes everted.

PRIOR ART

The introduction of elongated, flexible medical examination instruments, such as, for example, endoscopes, into body cavities which have a convoluted course, such as, for example, the intestine or the esophagus, involves difficulties and is not without risk for the patient. For this reason, there are many suggestions as to how this introduction can be improved.

A device for the introduction of an endoscope for intestinal diagnosis is described in German Offenlegungsschrift No. 2,823,025, which device comprises a pipe-like housing to whose distal opening is attached a thin-walled tube. This tube is inverted inside the housing and its other end is connected to the distal end of an endoscope. By applying a pressure medium to the housing, the tube everts out of the housing into the body opening, the endoscope being pulled after. As eversion proceeds, the tube covers the surface of the body cavity so that the endoscope does not come into contact with its walls during penetration into the body cavity. This procedure, which inherently imposes very little stress on the walls of the body cavity, has the disadvantage that the investigator is unable to inspect the walls of the body cavity through the endoscope until the tube has completely everted.

A very similar device described in U.S. Pat. No. 4,321,915 avoids this disadvantage by the tube being fixed not to the distal end of the endoscope but to a sleeve which can move sealingly on the endoscope. Since, when pressure is applied to the housing, the endoscope advances into the body cavity at twice the rate of the covering of the surface of the wall of the body cavity by the inverting tube, pressure and reduced pressure are applied alternately and the endoscope is withdrawn a little relative to the tube during the reduced pressure phases.

SUMMARY OF THE INVENTION

The object of the present invention is to make available an elongated, flexible medical instrument having a device to assist introduction by the principle of the eversible tube, which instrument is simpler to construct and use than those of the prior art. This has entailed making use of the recognition that it is unnecessary to assist the introduction of the medical instrument throughout the entire advance by the everting tube; on the contrary, for straightforward passages through body cavities, it suffices to advance the medical instrument in a conventional manner and to make use of the principle of the everting tube only with difficult passages.

The object is achieved by the device to assist introduction comprising a pipe which is open at both ends and has pressure connectors on the sides, and comprising a flexible, eversible tubular structure which runs through the pipe and whose two ends are each connected to one end of the pipe, the medical instrument running through the pipe inside the tubular structure and the tubular structure being folded in several double-layers in the region of the distal end of the medical instrument.

The item according to the invention is now used in such a manner that the medical instrument is applied to the body opening of the body cavity into which the introduction is to take place, and is advanced in a conventional manner until a curve or other hindrance is made noticeable by an increase in the resistance. Pressure is now applied to the instrument to assist introduction, and the medical instrument is advanced further, during which the first layer of the multilayer folding of the tubular structure unfolds in the region of the distal end of the medical instrument, that is to say it everts into the body cavity. This means that the medical instrument can easily be introduced further, in fact at double the rate of advance of the eversion front of the layer of the tubular structure which is everting. Apart from the medical instrument being easier to advance, the inversion of the tubular structure makes itself noticeable to the investigator by the fact that the proximal end of the medical instrument moves toward the proximal end of the device to assist introduction. After the hindrance has been overcome, the medical instrument is advanced further, again in the conventional manner, that is to say rubbing against the wall of the body cavity, until another hindrance makes itself noticeable. This and all other hindrances are overcome by applying a pressure medium to the device to assist introduction, and advancing the medical instrument using the inverting tubular structure. If during this the proximal end of the medical instrument approaches so close to the proximal end of the device to assist introduction that further eversion of the tubular structure under pressure is no longer possible, then the device to assist introduction can be pushed in the direction of the patient and the length of the tubular structure which is released by this can be pushed toward the distal end of the device to assist introduction, if necessary in several layers, and, if required, immobilized there by means of, for example, appropriate clamps.

The pipe-like part of the device to assist introduction, including the pressure connectors, is manufactured of metal or, where a disposable instrument is intended in order to avoid resterilization, of plastic such as, for example, polyamide or polyethylene. The tubular structure is manufactured of materials which are customary for thin-walled flexible structures of this type. Materials which are slightly permeable to the liquid pressure medium which is used prove to be particularly advantageous, such as, for example, cellulose acetate, because this means that the pressure medium can simultaneously act as a lubricant. The attachment of the ends of the tubular structure to the pipe of the device to assist introduction is carried out in a customary manner by bonding or sealing or other suitable means of attachment such as, for example, a shrinkable tube.

Liquids are particularly suitable as the pressure medium. When an aqueous medium is used, addition of, for example, glycerol or low viscosity liquid paraffin is advantageous to improve the lubrication.

An elongated medical instrument for the investigation or treatment of body cavities is to be understood to mean, in particular, endoscopes, biopsy instruments and irrigation devices for rectal, oral or nasal introduction. It is self-evident that the invention can also be applied usefully in other areas of the art where the problem of access for endoscopes and irrigation devices into non-linear cavities exists.

BRIEF DESCRIPTION OF THE DRAWING

FIG. 1 is a view, partly in section, of the medical instrument in accordance with the present invention, illustrated in the initial position;

FIG. 2 is a view, partly in section, of the instrument of FIG. 1, illustrated in a position in which the tubular structure of the instrument is partially everted;

FIG. 3 is a view, partly in section, of the instrument of FIG. 1, illustrated in a position in which the pipe surrounding the instrument has been advanced distally with respect to the instrument.

DETAILED DESCRIPTION OF THE INVENTION

FIG. 1 shows diagrammatically a medical instrument 9, which may be, for example, an endoscope for examination of the large bowel, in the initial position. The instrument 9 is pushed through the tubular structure 4 which runs through the pipe 2. The tubular structure 4 is attached in several double-layers in the distal region 10 of the instrument 9, so that the distal end 11 remains free. The tubular structure 4 fits just sufficiently snugly on the instrument 9 that it cannot be pushed back onto the instrument 9 during introduction into the body cavity. This fitting of the tubular structure 4 onto the instrument 9 is not represented in the drawing for reasons of clarity.

The proximal end 12 of the instrument 9 projects out of the tubular structure 4 since, when the instrument 9 is pushed in on application of pressure via pressure connectors 3, the proximal end 12 of the instrument 9 moves toward the inversion front 13 of the tubular structure 4. This is because, when the instrument 9 is pushed into the tubular structure 4, its inversion front 13 moves at only half the rate of the instrument 9.

FIG. 2 shows diagrammatically the instrument 9 in a position where the outermost double-layer 14 of the tubular structure 4 is partially everted due to the instrument 9 having been advanced on application of pressure via the pressure connectors 3. During this, the proximal end 12 of the instrument 9 moves in the direction of the pipe 2. In order to obtain more space to advance the instrument 9, it is possible to advance the pipe 2 in the distal direction with respect to the instrument 9.

FIG. 3 shows diagrammatically the instrument 9 in a position in which the pipe 2 has been advanced distally with respect to the instrument 9. The length of the tubular structure 4 which has been released on the distal side of the pipe by this is inverted onto the pipe 2 in each case. Several layers are inverted on depending on the length of the tubular structure 4 which is to be inverted on. The part of the tubular structure which has been inverted onto the pipe 2 is, if required, immobilized by suitable clamps (not shown in the Fig.). In order additionally to secure against slippage of the part of the tubular structure 4 which has been inverted onto the pipe 2, it is possible for the outside of the pipe 2 to have, for example, transverse corrugations.

In the case of an endoscope for examination of the large bowel, the instrument 9 has a length of, for example, about 2 m. The part of the tubular structure 4 which is attached in several, preferably two or three, double-layers to the distal region 10 of the instrument 9 has a length of approximately 20 to 40 cm. The length of the part of the tubular structure 4 which is attached in double-layers in the distal region 10 of the instrument 9 should correspond to at least the total of the lengths of the difficult passages which are to be expected on introduction. The proximal end 12 of the instrument should project beyond the proximal end 7 of the pipe 2 to an extent which corresponds to the total of the lengths of the difficult passages which are to be expected. It is advantageous in the initial position to set the distance between the inversion front 13 and the proximal end 7 of the pipe 2 at a maximum of one half of the distance between the proximal end 12 of the instrument 9 and the proximal end 7 of the pipe 2. The pipe 2 has a length of about 20 cm. Its internal diameter is somewhat larger than the external diameter of the instrument 9 at the distal end 11.

I claim:

1. An elongated medical instrument for the examination or treatment of body cavities, in particular endoscopes, with a device to assist introduction by the principle of the tubular structure which becomes everted, comprises the device to assist introduction (1) being composed of a pipe (2) which is open at both ends and has pressure connectors (3) on the sides, and is composed of a flexible, eversible tubular structure (4) running through the pipe (2), the two ends (5, 6) of the tubular structure each being connected to one end (7, 8) of the pipe (2), the medical instrument (9) running through the pipe (2) inside the tubular structure (4), and the tubular structure (4) being folded in several double-layers in the region (10) of the distal end (11) of the medical instrument (9).

* * * * *